United States Patent [19]

Goueli

[11] Patent Number: 6,066,462
[45] Date of Patent: May 23, 2000

[54] QUANTITATION OF INDIVIDUAL PROTEIN KINASE ACTIVITY

[75] Inventor: Said A. Goueli, Fitchburg, Wis.

[73] Assignee: Promega Corporation, Madison, Wis.

[21] Appl. No.: 09/280,047

[22] Filed: Mar. 26, 1999

Related U.S. Application Data

[63] Continuation of application No. 08/208,573, Mar. 4, 1994.

[51] Int. Cl.[7] .................. G01N 33/53; G01N 33/573; C07K 1/13; C12Q 1/48
[52] U.S. Cl. ..................... 435/7.1; 530/350; 435/7.4; 435/7.5
[58] Field of Search ................. 435/15, 23, 183, 435/193, 194, 7.1, 7.4, 7.5; 530/300, 326, 327, 328, 329, 330, 350

[56] References Cited

U.S. PATENT DOCUMENTS 4,923,802  5/1990  Gallis ........................................ 435/15
5,235,039  8/1993  Heath, Jr. et al. ....................... 530/328

OTHER PUBLICATIONS

Kemp. Design and Use of Peptide Substrates for Protein Kinases. Methods in Enzymology. 200: 121–134, 1991.

*Primary Examiner*—David Guzo
*Assistant Examiner*—Jon D. Shuman
*Attorney, Agent, or Firm*—DeWitt Ross & Stevens S.C.

[57] ABSTRACT

A method of quantitating the activity of a selected protein kinase on a peptide substrate is provided. The peptide substrate is conjugated to a binding compound. The modified peptide substrate is then added to a solution containing the selected protein kinase. The protein kinase and the peptide are incubated along with a label for sufficient time to form a modified peptide product having the binding compound and the label. The modified peptide product is then bound to a matrix having a high binding compound affinity. The bound peptide is then washed and the activity of the protein kinase is measured. Also provided is a kit for the stated method.

18 Claims, 5 Drawing Sheets

Vm = 1.45 pmol/min
Km = 33.5 μM

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 7 amino acids

```
            (B) TYPE: amino acid
            (D) TOPOLOGY: linear (ii) MOLECULE TYPE: peptide (xi) SEQUENCE DESCRIPTION: SEQ ID NO:1:

Leu Arg Arg Ala Ser Leu Gly
1               5

(2) INFORMATION FOR SEQ ID NO:2:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:2:

Ala Ala Lys Ile Gln Ala Ser Phe Arg Gly His Met Ala Arg Lys Lys
1               5                   10                  15

(2) INFORMATION FOR SEQ ID NO:3:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:3:

Arg Arg Arg Glu Glu Glu Thr Glu Glu Glu
1               5                   10

(2) INFORMATION FOR SEQ ID NO:4:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:4:

Pro Lys Thr Pro Lys Lys Ala Lys Lys Leu
1               5                   10

(2) INFORMATION FOR SEQ ID NO:5:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:5:

Asp Asp Asp Glu Glu Ser Ile Thr Arg Arg
1               5                   10

(2) INFORMATION FOR SEQ ID NO:6:

(i) SEQUENCE CHARACTERISTICS:
            (A) LENGTH: 15 amino acids
            (B) TYPE: amino acid
            (D) TOPOLOGY: linear (ii) MOLECULE TYPE: peptide
```

-continued (xi) SEQUENCE DESCRIPTION: SEQ ID NO:6:

Glu Pro Pro Leu Ser Gln Glu Ala Phe Ala Asp Leu Trp Lys Lys
1               5                   10                  15

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:7:

Asp Arg Val Tyr Ile His Pro Phe
1               5

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:8:

Arg Lys Ile Ser Ala Ser Glu Phe
1               5

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:9:

Arg Arg Arg Tyr Ser
1               5

(2) INFORMATION FOR SEQ ID NO:10:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:10:

Arg Arg Arg Tyr Ser Pro Thr Ser Pro Ser Tyr Ser Pro Thr Ser Pro
1               5                   10                  15

Ser Tyr Ser Pro Thr Ser Pro Ser Tyr Ser Pro Thr Ser Pro Ser
                20                  25                  30

QUANTITATION OF INDIVIDUAL PROTEIN KINASE ACTIVITY

This is a continuation of co-pending application Ser. No. 08/208,573, filed Mar. 4, 1994.

FIELD OF THE INVENTION

The invention is directed to a process for providing an assay protocol that measures enzymatic activity. More particularly, the invention is directed to a process to precisely and conveniently quantitate enzymatic activity of protein kinases and further to provide an assay specific for individual protein kinases in the presence of other protein. kinases.

CITED REFERENCES

A bibliography of the references cited in this application can be found in the section preceding the claims.

DESCRIPTION OF THE PRIOR ART

Enzymes are large proteins that catalyze reactions in living cells. Enzymes build up or tear down other molecules. For example, enzymes catalyze the synthesis of fat from fatty acids, form complex sugars from glucose and fructose, and aid in the formation of other proteins from amino acids. Enzymes also reverse the build-up process by breaking down more complex structures. Enzymes are generally specific to certain substrates for their reactions. For example, an individual enzyme may catalyze the reaction where only one substrate is involved or it may act on a group of related substrates.

In healthy persons, most enzymes are found within cells. Some diseases however cause the release of enzymes from dying cells into the blood. The increased levels of enzymes can then be measured. An abnormal level of enzymes in the blood characterizes certain medical conditions. For example, an enzyme assay for abnormal levels of the enzyme creatine kinase in the blood is useful as a diagnostic measure of heart disease. In like manner, bone or liver diseases can be diagnosed by observing increasing levels of alkaline phosphatase in the blood stream. Prostate cancer is diagnosed by increased levels of acid phosphatase in the blood stream.

Enzymes are classified into groups according to the general kind of reaction they catalyze. The present invention refers to a specific group of enzymes called transferases, which catalyze the transfer of a group from one substrate to another. The present invention is specifically directed to the transferase subgroup called protein kinases.

Protein kinase is a generic name for all enzymes that transfer a phosphate to a protein. About three to four percent of the human genome contains transcription information for the formation of protein kinases. Currently, there are up to 200 known different protein kinases. However, because three to four percent of the human genome is a code for the formation of protein kinases, there may be many thousands of distinct and separate kinases in the human body.

Protein kinases are enzymes which catalyze the transfer of phosphorous from adenosine triphosphate (ATP), or guanosine triphosphate (GTP) to the targeted protein to yield a phosphorylated protein and adenosine diphosphate (ADP) or guanosine diphosphate (GDP), respectively. ATP or GTP is first hydrolyzed to form ADP or GDP and inorganic phosphate. The inorganic phosphate is then attached to the targeted protein. The protein substrate which is targeted by kinases may be a structural protein, found in membrane material such as a cell wall, or another enzyme which is a functional protein.

Due to their physiological relevance, variety and ubiquitousness, protein kinases have become one of the most important and widely studied family of enzymes in biochemical and medical research. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis.

Protein kinases are often divided into two groups based on the amino acid residue they phosphorylate. The first group, called serine/threonine kinases, includes cyclic AMP and cyclic GMP dependent protein kinases, calcium and phospholipid dependent protein kinase, calcium and calmodulin-dependent protein kinases, casein kinases, cell division cycle protein kinases and others. These kinases are usually cytoplasmic or associated with the particulate fractions of cells, possibly by anchoring proteins.

The second group of kinases, called tyrosine kinases phosphorylate tyrosine residues. They are present in much smaller quantities but play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside.

Phosphorylation of serine-, threonine- and tyrosine-containing proteins by kinases is important because the phosphorylated protein products have been implicated in a variety of cellular processes including oncogenesis, cellular transformation, cellular growth and exocytosis. Currently, much experimentation is performed involving kinases which may inhibit cancer growth or promote cancer cell death. Determining the specific kinase involved in inhibiting cancer growth or promoting cell death is important to society. Therefore, advances in recognizing kinase activity levels are extremely important.

Activity Determination

Reference is made to Robyt and White (1990) which is incorporated herein by reference, for a general description of methods for determining the activity of an enzyme. Robyt and White defines the activity of an enzyme as the amount of reaction that a certain amount of enzyme will produce in a specified period of time. The activity is determined by measuring the amount of product produced or the amount of substrate used up per unit of time under high concentrations or saturating conditions of substrate. This is usually accomplished by performing a chemical analysis for the product or substrate.

Substrates that are typically used in an assay for specific kinase activity include casein, which is isolated from milk; histones, isolated from calves; phosphovitin, isolated from egg yolks; and myelin basic proteins, isolated from bovine spinal cords. These substrates can be phosphorylated in an assay, assuming that the correct kinase has been chosen. Assays utilizing these substrates to determine kinase activity are well known in the prior art.

Radioactive Detection of Kinase Activity

Most current methods of measuring protein kinase activity are based on the radioactive detection method. In these methods, a sample containing the kinase of interest is incubated with activators and a substrate in the presence of γ-$^{32}$P-ATP or γ-$^{32}$P-GTP. Often, a general and inexpensive substrate such as histone or casein is used. After a suitable incubation period, the reaction is stopped and an aliquot of the reaction mixture is placed directly onto a filter which binds the substrate. The filter is then washed several times to remove excess radioactively-labeled free ATP, and the amount of radio-labeled phosphate incorporated into the substrate is measured by scintillation counting. This method is widely used and provides an accurate method for determining protein kinase activity in both crude and purified samples.

Babcook et al. (1991) also describe an assay using monoclonal antibodies and immunofluorescence technology for the determination of protein-tyrosine kinase and protein-tyrosine phosphatase activities. The method was performed utilizing p56$^{lck}$ or p60$^{src}$.

Budde et al. (1991) disclose assay techniques utilizing acidic peptide substrates of protein kinases. This technology uses radioactive phosphorous placed in a substrate to be studied. After kinase activity, the phosphopeptide is eluted while the individual radioactive phosphorus, ATP and protein are impeded.

Gopalakrishna et al. (1992) disclose a method which utilizes the conventional approaches to measure protein kinase activity. The method combines the incubations and filtrations necessary to determine the protein kinase activity using multi-well plates with fitted filtration disks. In a related reference by Chakravarthy et al. (1990), kinase C activity is measured by using protein kinase C (PKC) selective peptide substrates by incorporating radioactive phosphorous into the substrate. The radioactivity is measured by liquid scintillation.

Non-Radioactive Determination of Kinase Activity

A non-radioactive method of detecting kinase activity has been developed in which tyrosine phosphorylation is detected by using anti-phosphotyrosine antibodies (Rijksen et al., 1991). After incubation of the tyrosine kinase with unlabeled ATP and a suitable substrate, the reaction mixture is subjected to a dot blot assay on a polyvinylidene diflouride (PVDF) membrane. The extent of phosphorylation is determined by reaction with anti-phosphotyrosine antibody, followed by detection with an immunogold staining procedure. The amount of phosphotyrosine present is detected with a densitometer.

A disadvantage of the dot blot method is that it is limited to detecting tyrosine kinases. Antibodies to phosphotyrosine can be produced due to the size of the antigen. Attempts to produce similar antibodies to phosphoserine and phosphothreonine have not been successfully employed to assay for phosphoserine- and phosphothreonine-containing proteins. In addition, the assay requires several incubation and washing steps, each taking a considerable amount of time, which results in a greatly extended assay completion time. The result of the assay is a colored dot on the blot. The colored dot may limit the effective sample range of the assay and may require the user to quantitate the final results using a scanning densitometer, which is an expensive piece of equipment not available in all laboratories. The densitometer must have beam dimensions covering at least the targeted cross section of the dots generated.

SUMMARY OF THE INVENTION

The present invention provides for a method of determining the presence or activity of a selected protein kinase, comprising conjugating a binding compound to a peptide substrate forming a modified peptide substrate; adding a sufficient quantity of the modified peptide substrate to a solution containing the selected protein kinase; incubating the protein kinase with the modified peptide substrate under conditions where the protein kinase is active for a time sufficient to form a modified peptide product; and measuring the activity of the protein kinase.

The present invention is further directed to a kit for determining the presence or activity of a selected protein kinase comprising a container containing a modified peptide substrate having specific reactivity to the protein kinase and modified by chemical reaction to allow quantitation; and instructions for use.

The present invention is also directed to a kit for determining the presence or activity of a tyrosine kinase comprising a container containing a modified peptide substrate selected from the group consisting of biotinylated Promega peptide G (SEQ. ID. NO: 7) and analogs and combinations thereof; a container containing a biotin-binding matrix; and instructions for use.

The present invention is also directed to a kit for determining the presence or activity of serine-threonine kinases comprising a container holding a modified peptide substrate selected from the group consisting of biotinylated Promega peptide A (SEQ. ID. NO: 1), biotinylated Promega peptide B (SEQ. ID. NO: 2), biotinylated Promega peptide C (SEQ. ID. NO: 3), biotinylated Promega peptide D (SEQ. ID. NO: 4), biotinylated Promega peptide E (SEQ. ID. NO: 5), biotinylated Promega peptide F (SEQ. ID. NO: 6), biotinylated Promega peptide G (SEQ. ID. NO: 7), biotinylated Promega peptide H (SEQ. ID. NO: 8) and analogs and combinations thereof; a container holding a biotin-binding matrix; and instructions for use.

Further, the present invention is directed to a method for detecting the presence or activity of a selected protein kinase in a body fluid comprising reacting the body fluid with a sufficient amount of a biotinylated peptide substrate forming a modified peptide product under conditions where the protein kinase is active for a time sufficient to form the modified peptide product in an amount such that the modified peptide product may be detected and measuring the amount of modified peptide product.

The present invention makes it possible to assay for a specific protein kinase in the presence of several other proteins kinases in a tissue extract. This type of assay is highly desirable to investigators because the purification of the specific protein kinase under study is not required. Conventionally, purification is required to remove other protein kinases in the extract. This lengthy approach may be circumvented by using the specific biotinylated peptide substrate approach.

In addition, the investigator is aided in determining the expression level of the specific kinase under various physiological conditions with minimal losses in the enzyme, since purification is obviated. This means that the activity assayed is an accurate estimate of the total active enzyme expressed.

Peptide substrates for several protein kinases such as cAMP-dependent protein kinase (PKA), cGMP-dependent protein kinase (PKG), Ca$^{2+}$/phospholipid-dependent protein kinases (PKC), casein kinases 1 and 2 (CK-1 and CK-2), growth factor receptors, non-growth factor receptors and soluble proteins that contain an active tyrosine kinase, cell cycle-dependent protein kinase (p34cdc2 protein kinase), S6 protein kinase, Ca$^{2+}$/calmodulin-dependent or multifunctional (CAM) protein kinases, DNA-dependent protein kinase, and carboxyl-terminal domain (CDT) kinases are custom synthesized using a peptide synthesis protocol that incorporates a biotinylated amino acid at the N-terminus of the peptide. Thus, there are several protein kinases that can be assayed by the present procedure providing for the ability to make several kits four use with the various protein kinases.

The assay is very fast and may typically be completed in less than 10 minutes after termination of the reaction. This is important since current protocols require approximately 2 hours to obtain the same objectives.

No special equipment is required other than standard equipment that is currently available in most laboratories. The procedure does not require special inorganic or organic solvents such as phosphoric acid, acetic acid, acetone or ethanol, found in prior art protocols.

The present invention is amenable to be adapted to a large scale assay which may be demanded by large laboratories or pharmaceutical laboratories engaged in drug research.

The cost of the present invention is similar to the cost of prior art assays. The projected increased cost of avidin and biotinylating reagent may be offset by the elimination of expensive solvents required by other assays.

Further, the present invention eliminates the need for the use of an assay system requiring gel electrophoresis to separate the exogenous peptide from endogenous substrates. Gel electrophoresis separates the various mono- and phosphorylated forms of the substrate that may be useful. However, this method further complicates the quantitation of total phosphate trsfer.

Problems are often encountered when utilizing the prior art filter binding paper assay to bind strongly positive molecules that are present in the tissue of cellular extract and are phosphorylated. The present invention overcomes the problems because only the substrate and product are bound since they are the only components that are biotinylated.

The present invention eliminates the need to change the primary structure of the consensus sequence, which is the primary amino acid sequence target of the enzyme being analyzed, by adding additional arginine residues in order to maintain the primary sequence for the enzyme that is present in vivo. Prior art assays utilizing filter binding require the substrates to contain multiple arginine residues which may alter the specificity of the substrate such that the substrate may become suitable for another kinase. An example of this alteration is given by the sequence Arg-Arg-Arg-Tyr-Ser (SEQ. ID. NO: 9) (a key to amino acid abbreviations is found in Table 1) that is present in the CDT kinase peptide substrate Arg-Arg-Arg(Tyr-Ser-Pro-Thr-Ser-Pro-Ser)$_4$ (SEQ. ID. NO: 10) which might be recognized by cAMP-dependent protein kinase and other kinases recognizing this sequence.

The present invention yields results with a greater probability of accuracy since virtually all of the phosphorylated peptide molecules are captured by the strong binding avidin or streptavidin-coated matrix. Conversely, the phosphorylated proteins aliquoted onto the phosphocellulous paper are bound by an electrostatic interaction that is not strong. Therefore, loss of phosphorylated peptide occurs during the washing procedure.

Reference is now made in detail to the preferred embodiments of the invention, examples of which are illustrated in the accompanying figures.

DETAILED DESCRIPTION OF THE INVENTION

Definitions

Figure 1:
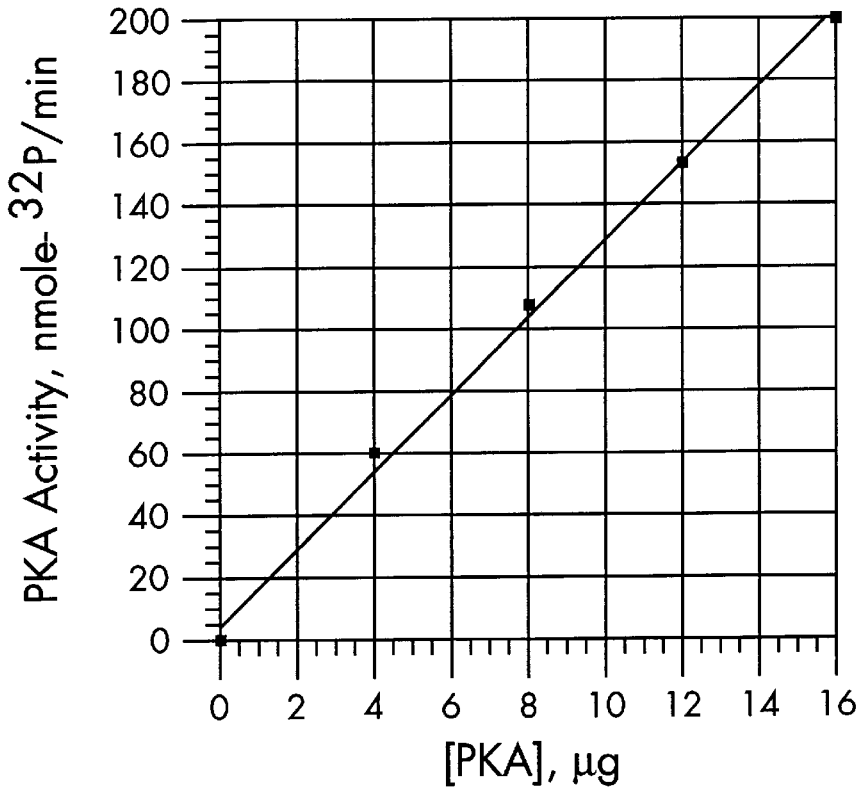
FIG. 1 is a graph illustrating the effect of enzyme concentration on the kinase activity of PKA using the modified Kemptide substrate. The peptide was present at 100 $\mu$M, and the enzyme was assayed as described in example 1.

For purposes of the present invention, the following definitions apply:

Activity of an enzyme: The amount of reaction product(s) that a certain amount of enzyme acting on a substrate will produce in a specified period of time.

Modified peptide: A chemical species composed of a peptide which has been subsequently reacted with a second chemical moiety, in this case biotin, which allows the peptide to be monitored by virtue of the properties of the second chemical moiety. The moiety may be referred to as a detector segment or modification tag.

Peptide: A compound generally consisting of 2–30 naturally occurring or synthetic amino acids which can also be further modified including covalently linking the peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds.

Phosphorylation: The addition of a phosphate group to a substrate.

Modified peptide product: A chemical species which is formed by the action of an enzyme on a modified peptide substrate, which has been altered from the original bonding pattern. Such alterations can include the addition or removal of new chemical species to the modified peptide substrate.

The particular changes made in the modified peptide substrate will depend upon the particular enzyme which has been involved in the alteration of the modified peptide substrate. Examples of a modified peptide product may include, but are not limited to, a product, formed by incubation of a modified peptide substrate with a protein kinase under conditions where the kinase has altered the modified peptide substrate by addition of a phosphate group to the peptide from a phosphate donor such as ATP or GTP.

Sequence requirement: The property of an enzyme to recognize and catalyze a reaction due to the peptide sequence of the substrate.

Substrate: The substance on which an enzyme acts.

Modified peptide substrate: A modified peptide which can be changed by the action of an enzyme. Such changes can include the addition or removal of chemical species to the modified peptide. Often it would be desirable to design a particular modified peptide substrate for assay of a particular enzyme of interest. A potential modified peptide substrate for protein kinase must have an amino acid which can act as a phosphate acceptor, such as serine. The utility of a potential modified peptide substrate for assay of a particular enzymatic activity can be determined by incubating the potential modified peptide substrate with the enzyme under conditions where the enzyme is known to be active and observing the rate with which a modified peptide product is generated.

The present invention quantitates the activities of kinase enzymes by measuring the amount of a specific modified peptide substrate that has undergone a reaction by the enzyme.

Kinases

The kinases quantified in the present invention preferably use ATP or GTP as the phosphate donor and transfer the gamma phosphate from the molecule to a serine, threonine or tyrosine amino acid. Protein kinases are distinguished by their ability to phosphorylate substrates on discrete sequences. These sequences have been determined by sequencing the amino acids around the phosphorylation sites and are usually distinct for each protein kinase. The recognition sequence on each substrate is for a specific kinase catalyst.

The substrate binding site on the kinase is believed to exist in the enzyme's catalytic domain. This domain is essential to all protein kinases. It typically contains over 240 residues and also contains the kinase's ATP or GTP binding site.

Measurement of Activity

The activity of an enzyme is determined by measuring the amount of product produced, i.e., modified peptide product. The measurement of the activity of the enzymes can be performed by quantitation of the amount of the tagged product of the reaction. The activity of protein kinases can be measured because of their capability to modify specific peptide substrates by addition of phosphate groups to the peptide substrates of the invention.

Incubation of Enzyme

The enzyme is incubated under conditions known to the art with the modified peptide substrate to form modified peptide products under conditions where the enzyme is active. Each of the enzymes is usually assayed at its optimum pH, temperature and other conditions.

Assay Protocol

An assay protocol has been developed to determine enzymatic activity of various protein kinases in a specific, fast and convenient manner. The assay protocol is intended to assay for individual protein kinases in the presence of a mixture of other protein kinases. The enzyme assay may be packaged in a kit format and separate kits can be provided for the specific protein kinase required. In addition, this assay may be scaled to accommodate a high through-put format.

Peptide Substrates

A number of specialized peptide substrates, including analogs and combinations of these peptide substrates, have been developed for use with the process, described in the following table:

TABLE 1

| Promega Peptide | Sequence | SEQ. ID. NUMBER |
|---|---|---|
| A | *-Leu-Arg-Arg-Ala-Ser-Leu-Gly | 1 |
| B | *-Ala-Ala-Lys-Ile-Gln-Ala-Ser-Phe-Arg-Gly-His-Met-Ala-Arg-Lys-Lys | 2 |
| C | *-Arg-Arg-Arg-Glu-Glu-Glu-Thr-Glu-Glu-Glu | 3 |
| D | *-Pro-Lys-Thr-Pro-Lys-Lys-Ala-Lys-Lys-Leu | 4 |
| E | *-Asp-Asp-Asp-Glu-Glu-Ser-Ile-Thr-Arg-Arg | 5 |
| F | *-Glu-Pro-Pro-Leu-Ser-Gln-Glu-Ala-Phe-Ala-Asp-Leu-Trp-Lys-Lys | 6 |
| G | *-Asp-Arg-Val-Tyr-Ile-His-Pro-Phe | 7 |
| H | *-Arg-Lys-Ile-Ser-Ala-Ser-Glu-Phe | 8 |

*Refers to Biotin $C_6$ moiety

Key:
| Abbreviation | Amino Acid |
|---|---|
| Ala | Alanine |
| Cys | Cysteine |
| Asp | Aspartic Acid |
| Glu | Glutamic Acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

Promega peptides A–C contain a favorable sequence specific for serine-threonine kinases. Promega peptide G forms a favorable substrate for the tyrosine kinase.

While the material presented takes advantage of peptides which are chemically synthesized in vitro and some of which are commercially available, it should be noted that the invention can be performed by isolation of a peptide from a natural source including digestion of a larger precursor protein or peptide and isolation of the proper resulting fragment by methods well known in the art followed by its attachment to a detector segment as defined.

The assay utilizes a biotinylated labeled peptide that is required for the protein kinase under consideration. In contrast to protein substrates often used for protein kinase assays, peptides can be designed to be a selective substrate for a particular kinase by synthesizing a peptide that mimics the consensus sequence recognized by the enzyme of interest. The biotinylated peptide can be phosphorylated by the respective protein kinase under optimal phosphotransferase conditions for that enzyme in the presence of $\gamma\text{-}^{32}\text{P-ATP}$. Since both the phosphorylated and unphosphorylated peptides are biotinylated, they can be captured on a biotin-binding matrix and the remaining free $\gamma\text{-}^{32}\text{P-ATP}$ can be removed by several washings.

The biotin-binding matrix can be any matrix that is covalently linked to avidin or streptavidin molecules such as filter disks, beads or a soluble matrix. FMC Corporation (Pine Brook, N.J.) is an example of a manufacturer of avidin and streptavidin in matrices such as Streptavidin-Linked Polyvinylcarbonate (PVC) Silica, Microporous Plastic Sheets or 12.5 mm Disks. The captured peptides may be placed in a liquid scintillation spectrometer to determine the $^{32}$P incorporated into the peptide and hence the protein kinase activity of the enzyme under consideration.

The basic principle of the biotinylated peptide approach is to conjugate the peptide substrates for a specific protein kinase with biotin from which the biotinylated peptide can be used as a substrate to assay for the enzyme in question. After completion of the reaction, the phosphorylated and unphosphorylated peptides are aliquoted onto streptavidin- or avidin-coated filter membranes, ELISA-formatted plates or avidin-coated magnetic particles, where the peptides bind. The free ATP can be removed by a washing procedure and the ATP-free peptides which are bound to the filters, particles or plates can then be counted in a liquid scintillation spectrometer, and the activity of the enzyme can be determined from the $^{32}$P incorporated. A biotin group may be successfully attached to a peptide to be used as a substrate for protein kinase activity measurement if the following criteria are met:

1. The biotin group must-be covalently linked to the N-terminal amino group and not to any other amino group present internally or C-terminally to the peptide substrate. This is essential since linking a biotin molecule covalently to an ϵ amino group of an internal lysine will result in an alteration of the overall peptide charge. Hence, the effectiveness of the peptide as a substrate for some protein kinases such as PKA, PKC and CAM kinases may be altered.

2. The addition of the biotin moiety to the peptide should not result in a steric hindrance of the peptide substrate's accessibility to the enzyme under investigation. Preferably, six carbon atoms link the biotin to the substrate to minimize steric hindrance.

3. A matrix that can bind the biotinylated phosphorylated peptide must be made available so that the activity of the protein kinase in question may be determined by measuring the amount of radio-labeled peptide product. The binding should be specific for the modified phosphopeptide and any phosphorylated proteins or other peptide present in a sample should not bind to the matrix. Thus, the activity is proportional to the amount of bound phosphorylated, biotinylated peptide.

4. The excess γ-$^{32}$P-ATP that was not used in the reaction should be completely removed. The objective is to promote a low background noise level and further, to provide a quick method to assay for the enzyme in question.

5. The binding capacity of the matrix to the biotinylated peptide should be high enough such that a concentration several times the Km value for the peptide substrate is used. This requirement will ensure that the initial rate of reaction is linear within a reasonable time. Further, the initial rate of reaction should be proportional to the amount of enzyme in the reaction.

For small scale experiments, a 25 mm diameter avidin-coated membrane disk can be numbered with a pencil. Alternatively, a known volume of avidin-coated magnetic particles in an Eppendorf tube may be used.

Kinase Assay

The kinase assay is carried out as described using purified enzymes or tissue extracts as an enzyme source and the biotinylated peptide as a substrate in the presence of other reagents that are required for the reaction such as buffer, divalent cations such as $Mn^{2+}$, $Ca^{2+}$, and $Mg^{2+}$, and γ-$^{32}$P-ATP. For some protein kinases, other cofactors may be required such as phospholipids and calmodulin. After completion of the reaction, an aliquot is withdrawn and applied directly to the avidin-coated disks. The disks are placed in a beaker containing 2M NaCl to wash the free γ-$^{32}$P-ATP. Alternatively, the aliquots are pipetted into the particles-containing tube and mixed well. The NaCl in the beaker can be changed 5 times each for 1 minute, which completes the operation in 5 minutes. When particles are used they may be washed by conventional means to remove free soluble reaction components including ATP and endogenous proteins.

The assay may be scaled up to a high through-put assay by slight modification of the matrix. Twenty-four or 96 wells containing streptavidin-coated plates may be used. Aliquots, withdrawn after completion of the assay reaction, are pipetted directly into individual wells rather than onto individual disks. Subsequently, the whole plate is washed by rinsing the wells with 2M NaCl. It is noted that prior art devices are available to apply the completed reaction mixture to the individual wells. Washing of the wells may be accomplished with an automated system. The plates may then be counted by using a liquid scintillation spectrometer such as a Top Count Microplate Scintillation and Luminescence Counter manufactured by Packard Corporation in Meriden, Connecticut and Wallac, Inc., in Gaithersburg, Maryland. Non-limiting examples of assays utilizing the present invention follow.

cAMP-Dependent Protein Kinase (PKA)

When cAMP-dependent protein kinase (PKA) is under investigation, a peptide substrate that is reported to be specific for this enzyme is biotinylated on its N-terminal group. A modified peptide *-Lys-Arg-Arg-Ala-Ser-Leu-Gly (Promega Peptide A; SEQ. ID. NO: 1) is synthesized using a peptide synthesizer. The peptide is tested by methods known to the art for being a substrate for PKA at different concentrations; namely, 0, 10, 20, 50 and 100 μM with purified PKA at several dilutions. The enzyme used in the studies is the catalytic subunit of PKA (#V5161, Promega Corporation, Madison, Wis.) with a specific activity of 50 pmol $^{32}$P transferred to casein per μg enzyme in 1 minute at 37° C. or 10,000 pmol $^{32}$P transferred to the Kemptide substrate Lys-Arg-Arg-Ala-Ser-Leu-Gly (Promega Peptide A, SEQ. ID. NO: 1) per μg enzyme per minute at 37° C.

Phosphotransferase Activity of Protein Kinases

This assay tests for determining the phosphotransferase activity of other protein kinases using the corresponding biotinylated peptide substrates. For example, to assay for the kinase activity of $Ca^{2+}$ and phospholipid-dependent protein kinase (PKC), biotinylated neurogranin-derived peptide *-Ala-Ala-Lys-Ile-Gln-Ala-Ser-Phe-Arg-Gly-His-Met-Ala-Arg-Lys-Lys (Promega Peptide B; SEQ. ID. NO: 2) is used as a substrate under optimal condition for PKC protein kinase activity.

Other Assays

Other protein kinases can be assayed as described above for PKA and PKC but employing the appropriate peptide substrates and assayed under the corresponding optimal assay conditions. For example, the peptide substrate, *-Asp-Asp-Asp-Glu-Glu-Ser-Ile-Thr-Arg-Arg (Promega Peptide E, SEQ. ID. NO: 5) is used to assay for casein kinase I (CK-1). The peptide *-Arg-Arg-Arg-Glu-Glu-Glu-Thr-Glu-Glu-Glu (CK-2) (Promega Peptide C, SEQ. ID. NO: 3) is used to assay for casein kinase II (CK-2). The peptide,

*-Asp-Arg-Val-Tyr-Ile-His-Pro-Phe (Promega Peptide G, SEQ. ID. NO: 7) is used to assay for the tyrosine kinase activity of activated epidermal growth factor receptor (EGFR).

In each case, the enzyme activity of the protein kinase under study is assayed using the method that was developed using the biotinylated derivative of the appropriate peptide substrate and the streptavidin-linked matrix, and then by the phosphocellulose disk method using an unmodified peptide substrate.

Protein kinases are assayed under their optimal conditions as described below with the exception of using the unmodified peptide substrates in the reaction and the recommended processing procedure described in Casnellie, J. E., 1991. Briefly, the reaction is terminated by withdrawing 40 µL aliquots and spotting them onto P81 paper (Whatman, Clifton, N.J.). The filters are dropped immediately into a beaker containing 0.5% phosphoric acid, and they are left with occasional swirling of the beaker for 5 minutes. The phosphoric acid solution is decanted and a fresh solution is added. This step is repeated again for a total of 4 washes, each for 5 minutes. The filters are dried and placed in scintillation vials and 5 ml of scintillation fluid was added. Enzyme activity is determined as described above in the assay system.

To determine the protein kinase activity for various kinases, certain criteria have to be met as follows:

1. The biotinylated derivative of the peptide should serve as a specific and good substrate for the enzyme in question as the unmodified peptide substrate.

2. The phosphorylation of the biotinylated peptide should not affect its binding to the avidin-linked matrix or to the streptavidin-linked matrix.

3. The phosphorylation of the biotinylated peptide should be proportional to the amount of the enzyme added and to certain time periods of the assay.

4. The phosphorylated proteins should not bind to the matrix unless they are biotinylated, i.e., only the phosphorylated and biotinylated peptide should be bound to the matrix.

5. The avidin-linked or streptavidin-linked matrix should have enough binding capacity for the biotinylated peptide added to the matrix.

6. There should be a means to remove the free, excess $\gamma$-$^{32}$P-ATP after completion of the reaction.

To achieve these criteria, peptides are synthesized that are specific substrates for several protein kinases (Kemp, B. E. and Pearson, R. B., 1991). Each of these peptides contain the consensus sequence required for phosphorylation by the corresponding enzyme. It is usually necessary to have these peptides linked to basic amino acids to impart a positive charge(s) on the peptide so that it may bind to the negatively charged phosphocellulose paper.

In the present invention, the peptides are modified in a manner that makes them tightly bound to the matrix. The biotinylated moiety is linked to the $NH_2$ terminal of the peptide substrate via a 6-carbon atom linker.

The biotin-modified peptides are synthesized on a peptide synthesizer using established procedures of solid-phase peptide synthesis (Nova Biochem/Calbiochem, San Diego, Calif.). The biotin group is added before cleavage of the peptide from the resin. The identity and purity of the biotinylated peptides are confirmed by quantitative amino acid analysis, 2 high pressure liquid chromatography (HPLC) solvent systems, and fast atom bombardment (FAB) mass spectrometry.

Several parameters are investigated that may have influenced or affected the results of this assay. These are the diameter of the disks, the density of streptavidin per disk, the level of drying of the disks, the concentration of the modified peptide substrate and the amount of enzyme that can be used.

The assay is carried out at 37° C. for 5 minutes. A proportional increase in the kinase-activity to the increase in the amount of enzyme present is observed.

Silica-based filter disks are manufactured that are linked to avidin or streptavidin. Two different sizes are made. One is 25 mm (i.d.) and the other was 12.5 mm (i.d.). The filters are linked to 0.5, 1.0, or 2.0 mg of streptavidin or avidin. The 12.5 mm diameter disks with 0.5 mg streptavidin per disk give the best results. In addition, several levels of dryness are tested such as wet, 1 hour dried disks, 2 hour dried disks, and 2 week dried disks for their suitability in this assay. This is examined to ensure that the assay is user friendly. Results indicate that semi-wet as well as dry disks can be used successfully in this assay.

The specificity of this assay is further examined by using tissue extract as a source of PKA. The linearity of $^{32}$P incorporation into the biotinylated peptide is also checked by increasing the substrate concentration.

Experimental results indicate that the biotinylation of the peptide substrate does not affect the suitability of the peptide as substrate. One mg of avidin (or streptavidin) per disk of 25 mm (i.d.) (0.5 mg/disk of 12.5 mm (i.d.) is sufficient for the binding of up to 5 nmol of biotinylated peptide which gives a final concentration of 200 µM (reaction vol of 25 µL). This peptide concentration is sufficient for most of the purposes required. Both avidin and streptavidin can be used for this assay, and due to the lower cost of streptavidin, most of the studies are performed with streptavidin.

Finally, all wash solutions are tested to remove the free ATP and the best background is obtained with 2M NaCl. Thus, this solution was used as the wash solution.

The following conditions were carried out to generate data:

1. Reactions were terminated with the termination solution (2M urea, 125 mM EDTA, and 1% SDS), and 25 µL aliquots were spotted onto 12.5 mm streptavidin-linked disks (0.5 mg of streptavidin) or into wells of the 24-well plate.

2. The disks or wells were rinsed or washed five times each for one minute with 2M NaCl.

3. The disks or plates were dried and counted using a liquid scintillation counter.

Kits

The present invention is also directed to kits that utilize the process described. A basic kit for quantitating the activity of an enzyme includes a container containing a bioreagent, which is a modified peptide substrate having specific reactivity to the enzyme, modified by chemical reaction to allow quantitation, and instructions for use.

The modified peptide substrate supplied in the kit includes the binding compound biotin. The kit also contains at least one buffer which is compatible with the enzyme selected.

A kit is directed to specifically detect activity from enzymes selected from the group of serine-threonine kinases and tyrosine kinases. The kit includes a container holding a modified peptide substrate with the binding compound biotin attached. The substrate modified peptide is specific for the selected enzyme.

A kit is directed to quantitating the activity of an enzyme which is selected from the group consisting of kinases. The basic kit includes at least one container with a modified peptide substrate including the binding compound biotin. The substrate modified peptide is specific for the selected enzyme.

The modified peptide substrate in the kit may be one of the following peptides, depending upon the type of enzyme to be assayed as explained: Promega Peptide A (SEQ. ID. NO: 1), Promega Peptide B (SEQ. ID. NO: 2), Promega Peptide C (SEQ. ID. NO: 3), Promega Peptide D (SEQ. ID. NO: 4), Promega Peptide E (SEQ. ID. NO: 5), Promega Peptide F (SEQ. ID. NO: 6), Promega Peptide G (SEQ. ID. NO: 7) and Promega Peptide H (SEQ. ID. NO: 8). Reference is made to Table 1 indicating modified peptide substrates specific for selected enzymes.

Instructions for use are also included. "Instructions for use," is a tangible expression describing the reagent concentration or at least one assay method parameter such as the relative amount of reagent and sample to be admixed, maintenance time periods for reagent/sample admixtures, temperature, buffer conditions and the like.

The kit may also include a biotin-binding matrix linked to avidin or streptavidin molecules such as filter disks, beads, soluble matrix or plates. The biotin-binding matrix may be utilized to bind the modified peptide substrate and modified peptide product containing biotin.

The amounts of the various reagents in the kits can be varied depending on a number of factors, such as the optimum sensitivity of the assay. The instructions for use are suitable to enable an analyst to carry out the desired assay.

It is within the scope of this invention to provide manual test kits or test kits for use in automated analyzers.

The following examples are presented to illustrate the advantages of the present invention and to assist one of ordinary skill of making and using the same. The examples are not intended in any way to otherwise limit the scope of the disclosure or protection granted by the patent. While precise descriptions are given for assays of protein kinases, it should be clear to one well versed in the art that the results of the present invention can be applied to the assay of a wide variety of selected enzymes.

While the material presented takes advantage of peptides which are chemically synthesized in vitro, and some of which are commercially available, it should be noted that the invention can be performed by isolation of a peptide from a natural source.

EXAMPLES

The assays in these examples are based on the use of biotinylated peptide substrates that are specific for certain enzymes.

Example 1
Kinase Activity of cAMP-Dependent Protein Kinase

The kinase activity of cAMP-dependent protein kinase (PKA) was carried out in duplicates at each of the various peptide substrate concentrations, in a reaction volume (50 $\mu$L) containing 40 mM Tris HCl, pH 7.4, 20 mM $MgCl_2$, 100 $\mu$M $\gamma$-$^{32}$P-ATP (sp.act. of 100–200 cpm/pmol), 100 $\mu$g/ml of bovine serum albumin (BSA), and the appropriate biotinylated peptide substrate: *-Leu-Arg-Arg-Ala-Ser-Leu-Gly (Promega Peptide A, SEQ. ID. NO: 1, M.Wt of 998.4).

The reaction was started by addition of the appropriate amount of enzyme (Promega #V5221) to give 2 Kemptide units and incubated for 0, 5, and 10 minutes at 37° C. (one Kemptide unit is defined as the amount of enzyme required to catalyze the incorporation of 1 pmol of phosphate into Kemptide substrate in 1 minute). At specified periods of time at the appropriate temperature, the reaction was terminated with the addition of 10 $\mu$L of terminating solution as described above.

Twenty-five $\mu$L aliquots were withdrawn and spotted in a 12.5 mm (i.d.) streptavidin-linked disk (0.5 mg of streptavidin/disk) and placed in 2M NaCl-containing beaker. After one minute of gently swirling the beaker at room temperature, fresh NaCl was added. This washing procedure was repeated 5 more times at one minute each. The disks were then washed once more with water, dried and placed in scintillation vials. Five ml of scintillation fluid was then added.

Enzyme activity was calculated by determining the radioactivity via liquid scintillation spectrometry. To confirm that the phosphorylation was specifically catalyzed by PKA, a specific and potent inhibitor of PKA (#V5681, Promega Corporation, Madison, Wis.) was included in the reaction. All PKA phosphotransferase activity should have been inhibited by the addition of inhibitor.

Results Using Measured PKA

The relationship between rate of reaction (initial velocity of PKA) as determined by the protocol and under the condition described above, and the amount of enzyme in the reaction is shown in FIG. 1. Using 100 $\mu$M of modified peptide substrate in the reaction, a linear response in the activity of PKA was obtained with increasing the amount of enzyme in the reaction. The activity of the enzyme was also investigated in relation to the concentration of the biotinylated peptide substrate.

Figure 2:
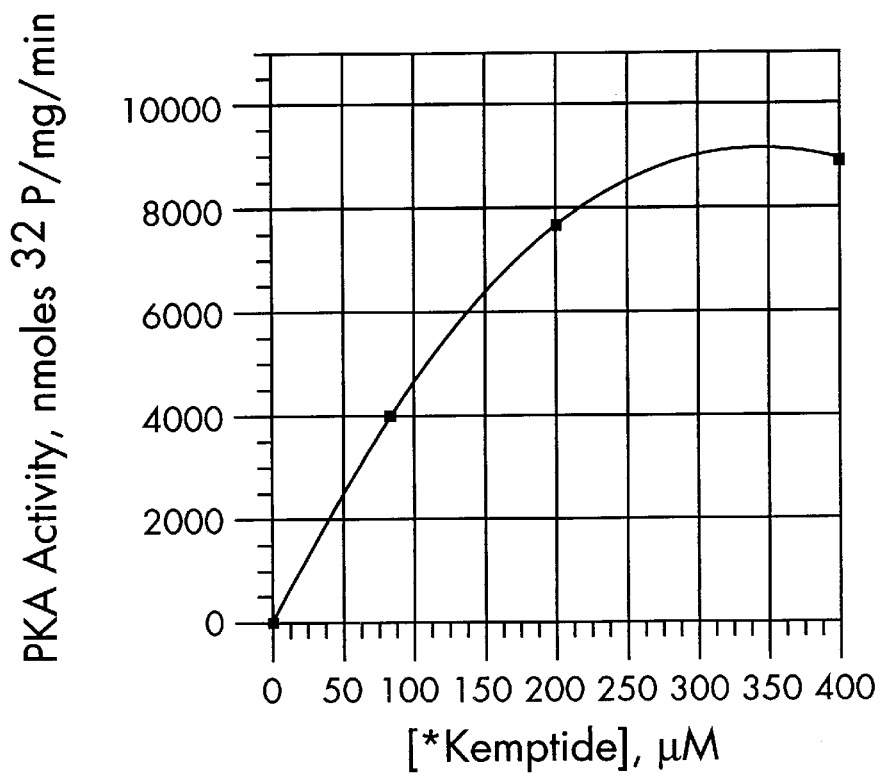
FIG. 2 is a graph illustrating the effect of increasing the concentration of the biotinylated Kemptide substrate on the protein kinase activity of PKA. Two Kemptide units of PKA were present in the reaction. The remaining reaction components were present as described in example 1.
Figure 3:
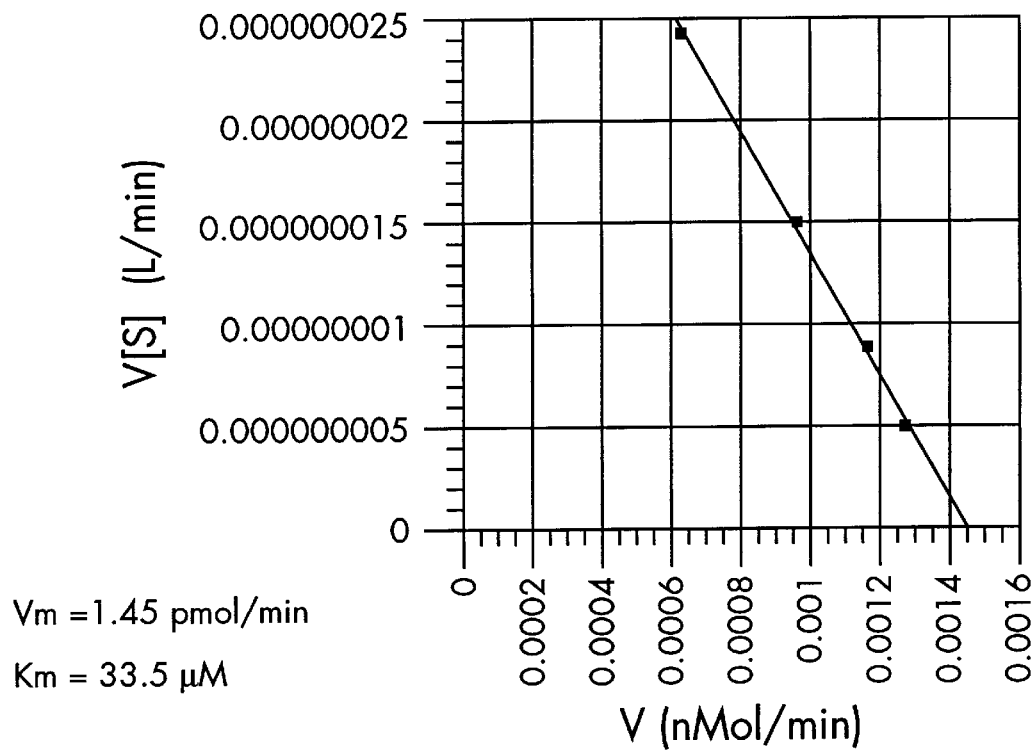
FIG. 3 is a graph illustrating the kinetic analysis of PKA with Kemptide as a substrate at 2 units per reaction as described in example 1.
Figure 4:
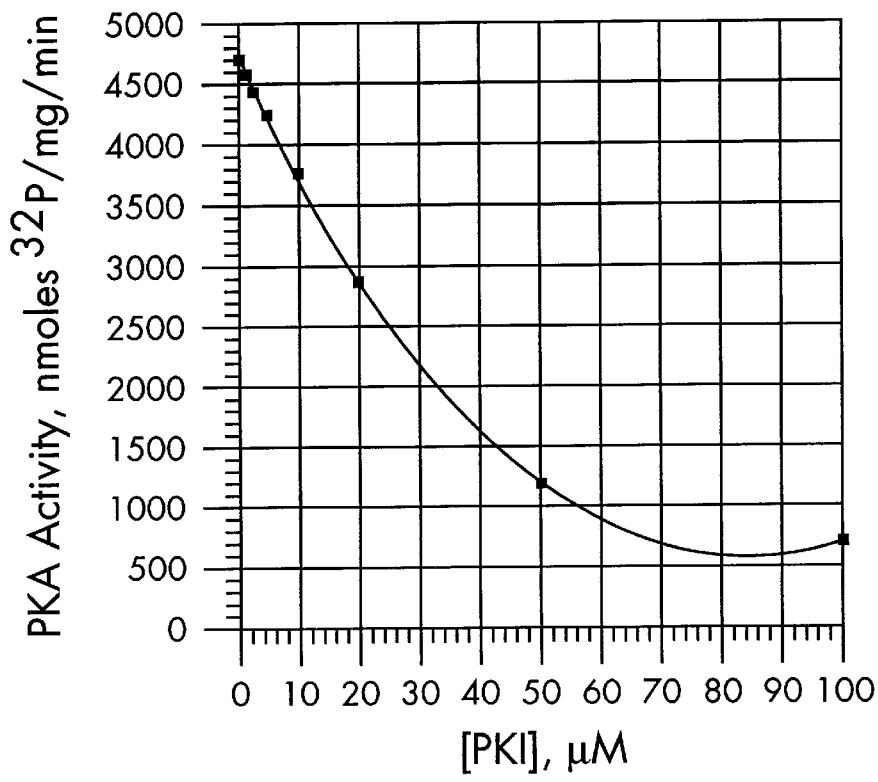
FIG. 4 is a graph illustrating the effect of the peptide inhibitor of PKA on its protein kinase activity as described in example 1.

As shown in FIG. 2, the kinetic plot displays typical Michaelis-Menten saturation behavior (hyperbolic curve). The transformation of the same data resulted in a Km Value for the substrate of 33 $\mu$M, and a Vmax value of 1.45 pmol/min as illustrated in FIG. 3. Similar values were obtained with the phosphocellulose paper assay using the Kemptide as substrate, and a Km value for the unmodified substrate was not affected by biotinylation as illustrated in FIG. 4. Kemp, B. E. and Pearson, R. B. 1991. The protein kinase activity was specific to PKA since the addition of 50 $\mu$M of the PKA inhibitor-(PKI) drastically reduced the enzyme activity.

Example 2
Kinase Activity of PKA in Rat Tissues

The kinase activity of PKA in various rat tissues was also investigated using the modified peptide substrate and assay protocol as described above.

Figure 5:
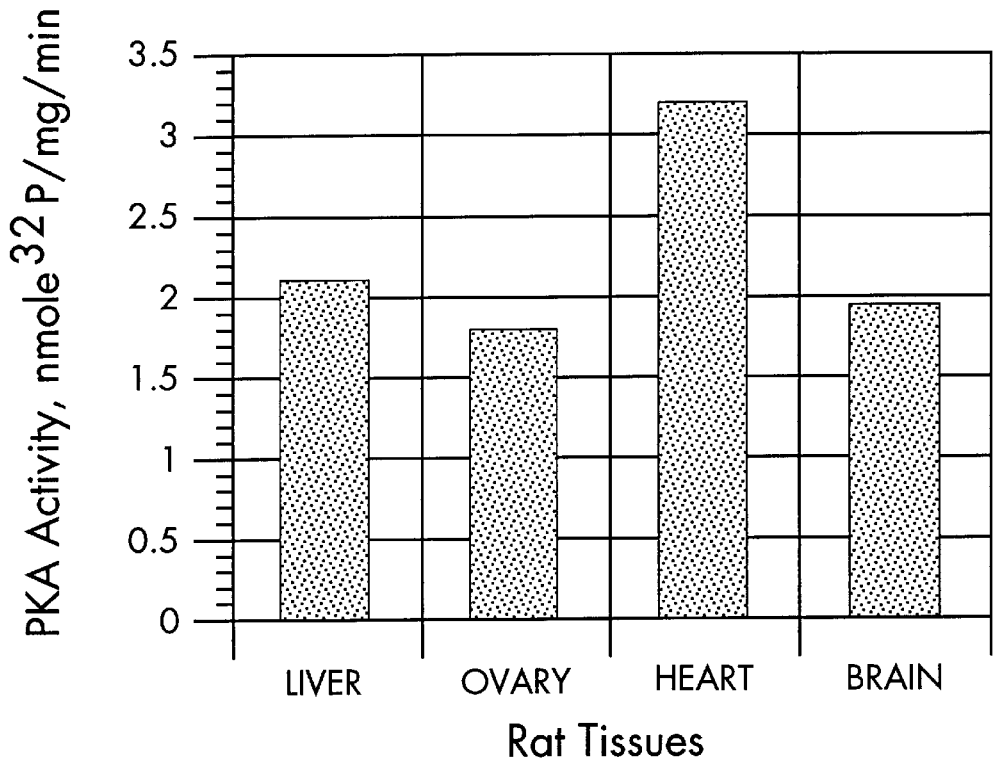
FIG. 5 is a graph illustrating the protein kinase activity of PKA in various rat tissues as described in example 2.

As illustrated in FIG. 5, the protein kinase activity of PKA was 2.2, 1.75, 3.2, and 1.9 nmol $^{32}$P/min/mg of rat liver, ovary, heart, and brain, respectively, and was comparable to those obtained with unmodified peptide and the phosphocellulose paper method. The phosphate incorporation into the modified substrate was completely abolished when 100 $\mu$M of PKA inhibitor (PKI) was included in the reaction. Thus, the phosphorylation of the modified peptide substrate, under the conditions described above and assayed with the protocol, is catalyzed by PKA and not by other protein kinases present in the tissue extract.

Any protein(s) that is phosphorylated in the reaction and has a basic charge will not bind to the matrix. Only the phosphorylated modified peptide substrate is bound to the matrix. Thus, the phosphate incorporation using the assay protocol reflects the true $^{32}$P incorporation into the peptide substrate. This is not the case with the phosphocellulose paper assay method where any basic protein in the extract that is phosphorylated will bind to the paper and results in overestimation of the kinase activity of the enzyme.

Example 3
Protein Kinase Activity of $Ca^{2+}$ and Phospholipid Dependent Protein Kinase The protein kinase activity of $Ca^{2+}$ and phospholipid dependent protein kinase activity (PKC) was determined in a similar manner to that of PKA described above, except that the biotinylated peptide substrate was a derivative of neurogranin; namely, biotinylated neurogranin $_{(28-43)}$ Chen, S-J, et al., 1993.

The peptide was modified by the addition of biotin containing moiety: *-Ala-Ala-Lys-Ile-Gln-Ala-Ser-Phe-Arg-Gly-His-Met-Ala-Arg-Lys-Lys (Promega Peptide B, SEQ. ID. NO: 2, Mol.Wt. is 2139.6), and was used at a concentration of 100 μM. The enzyme (#V5261, Promega Corporation) was diluted 5× in 100 μg/ml of BSA.

The kinase activity of the PKA was determined in a reaction volume of 50 μL consisting of 40 mM Tris. HCl, pH 7.4, 10 mM MgCl$_2$, BSA at 100 μg/ml, and 100 μM of γ-$^{32}$P-ATP (sp.act. of 100 cpm/pmol). The activity was determined in the presence and absence of 100 μg/ml of phosphatidylserine, 10 μg/ml of diacylglycerol and 0.4 mM calcium chloride. Reaction was started with the addition of 5 μL of the enzyme and incubated at 25° C. After specified periods of time, reactions were terminated by the addition of 10 μL of terminating solution (see above). Twenty-five μL aliquots were aliquoted on disks and the disks were processed as described above for PKA.

Results Using Measured PKC

Figure 6:
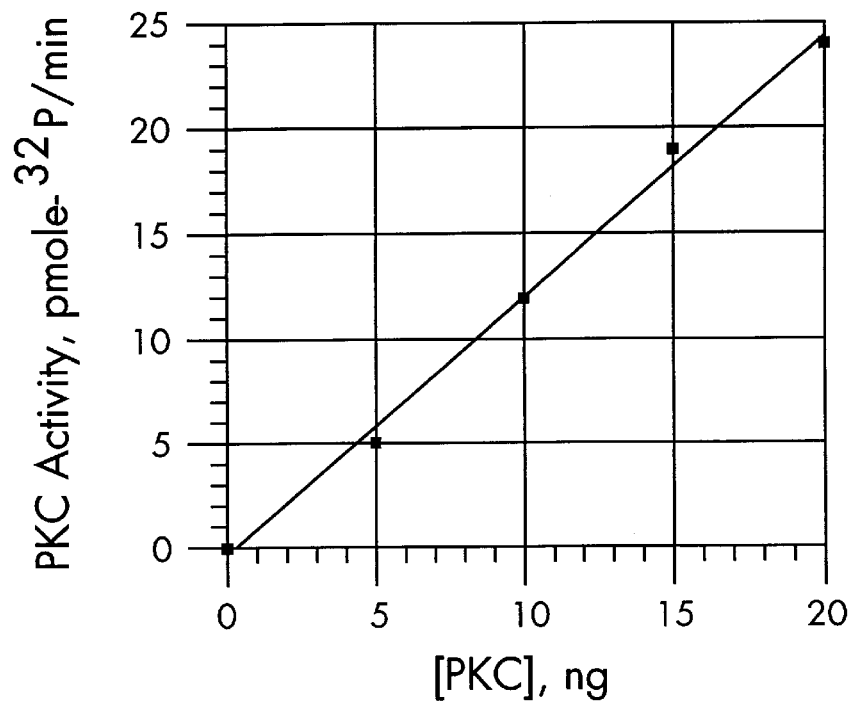
FIG. 6 is a graph illustrating the effect of enzyme concentration on the kinase activity of PKC using the biotinylated neurogranin $_{(28-43)}$ as substrate as described in example 3.

The activity of PKC obtained was also compared with that obtained using the unmodified peptide substrate and assayed by the phosphocellulose paper method. The results shown in FIG. 6, using a modified peptide substrate concentration of 100 μM, indicate that the PKC activity was linear with increasing the amount of enzyme protein in the reaction. Similar to the work presented with PKA, the effect of substrate concentration on the kinase activity of PKC was also investigated.

Figure 7:
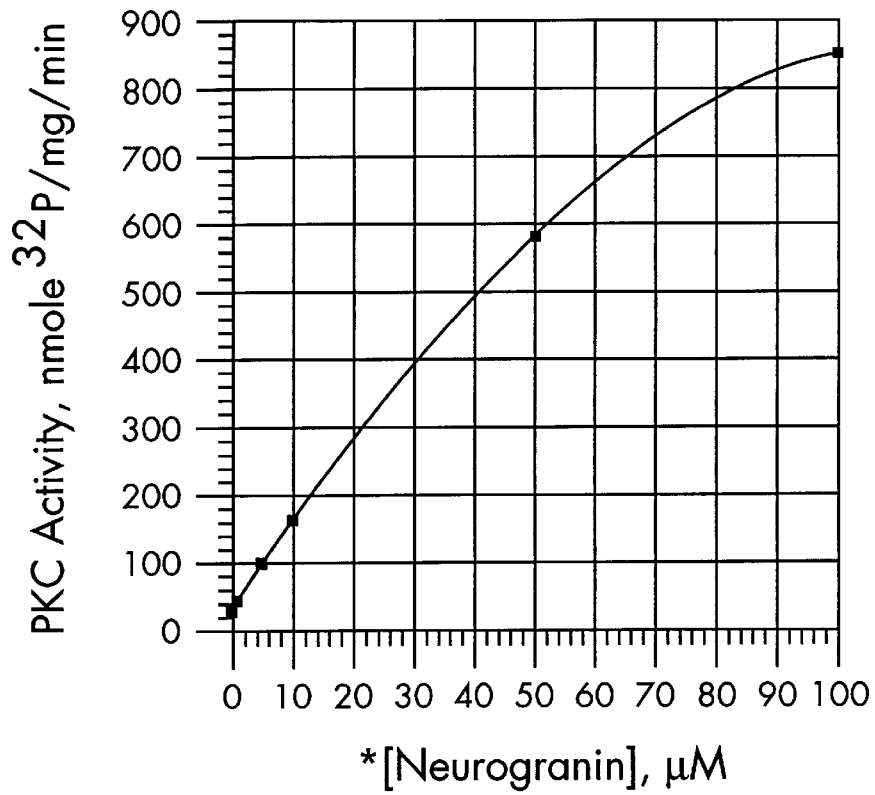
FIG. 7 is a graph illustrating the effect of increasing the concentration of the biotinylated neurogranin $_{(28-43)}$ substrate on the protein kinase activity of PKC as described in example 3.

A Michaelis-Menten kinetics was obtained, i.e., hyperbolic curve as illustrated in FIG. 7, and the activity of the enzyme reached a maximum around 100 μM of modified substrate. However, the activity of PKC was about 6–7 fold higher than its activity when assayed with the phosphocellulose paper method. The increase in activity of PKC in the assay system may be due to the enhanced and specific binding of the phosphorylated peptide and also to the small loss of the phosphorylated peptide product from the matrix during the washing procedure. This demonstrates that the kinase activity of the enzyme can be determined accurately by using the assay system with the biotinylated neurogranin $_{(28-43)}$.

Figure 8:
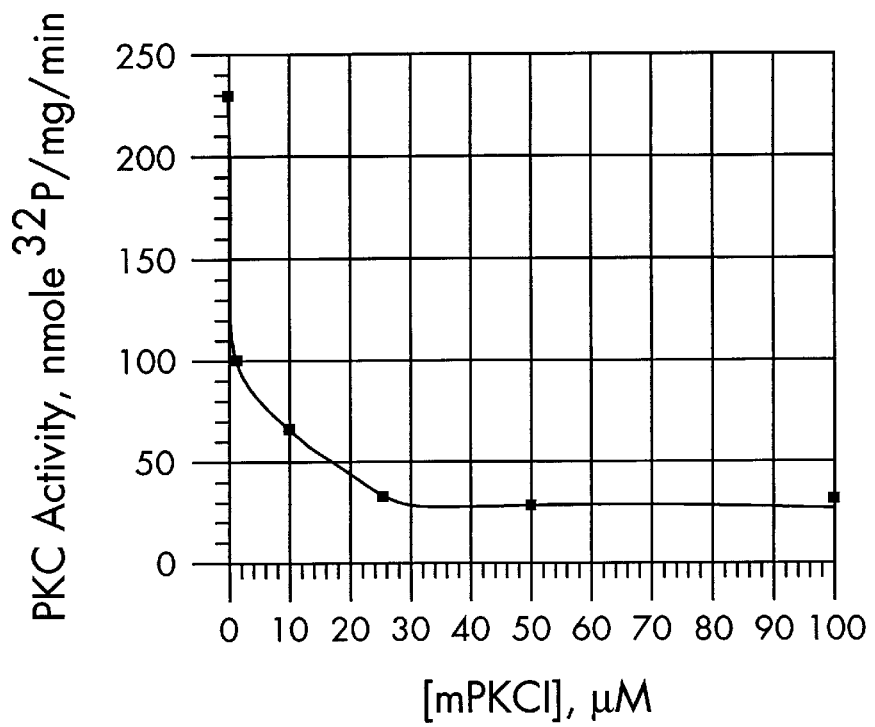
FIG. 8 is a graph illustrating the effect of the PKC inhibitor on the activity of PKC using the biotinylated neurogranin $_{(28-43)}$ as a substrate as described in example 3.

The activity was fully inhibited by the specific myristoylated PKC peptide inhibitor as illustrated in FIG. 8. Therefore, 10–20 μM of the inhibitor was sufficient to inhibit the kinase activity of PKC, indicating that all incorporated $^{32}$P into the peptide substrate was catalyzed via PKC.

Example 4
Kinase Activity of PKC Using Rat Tissue

The kinase activity of PKC in the rat brain was also studied utilizing the materials and methods of Example 3.

Figure 9:
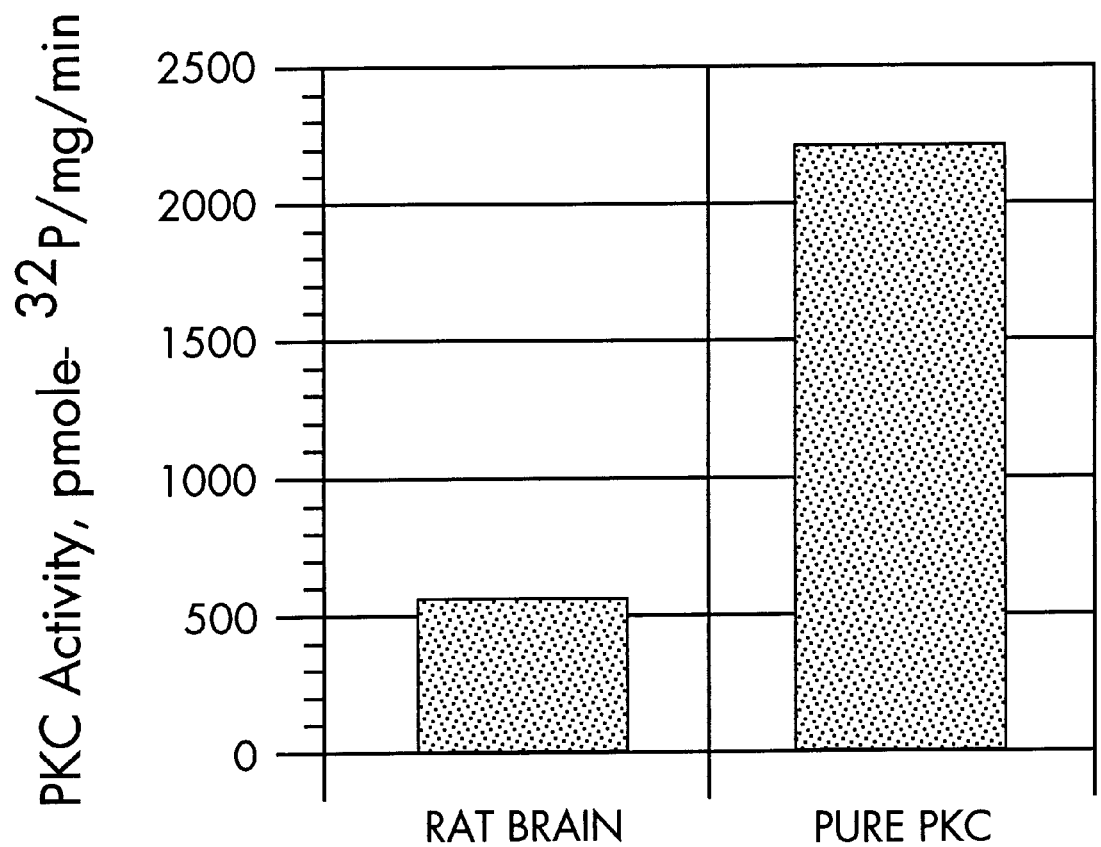
FIG. 9 is a graph illustrating the effect of protein kinase activity of PKC in rat brain extract and of a partially pure PKC as described in example 4.

As illustrated in FIG. 9, the activity of PKC in an enriched fraction of a high spin supernatant of rat brain extract was about 500 pmol $^{32}$P/mg/min, and that of partially purified PKC was 2200 pmol $^{32}$P/mg/min.

It is understood that the invention is not confined to the particular construction and arrangements herein illustrated and described, but embraces such modified forms thereof and comes within the scope of the claims following the bibliography.

Bibliography of Cited References

Babcook, John, Julian Watts, Ruedi Aebersold and Hermann J. Ziltener, 1991, "Automated Nonisotopic Assay for Protein-Tyrosine Kinase and Protein-Tyrosine Phosphatase Activities." Anal. Biochem., 196, 245–251.

Budde, Raymond J. A., John S. McMurray and Donald A. Tinker, 1992, "An Assay for Acidic Peptide Substrates of Protein Kinases." Anal. Biochem., 200, 347–351.

Casnellie, J. E., 1991. "Assay of Protein Kinases Using Peptides with Basic Residues for Phosphocellulose Binding." Meth. Enzymol., 200:115–120.

Chakravarthy, Balu R., Alexandra Bussey, James F. Whitfield, Marianna Sikorska, Ross E. Williams and Jon P. Durkin, 1991, "The Direct Measurement of Protein Kinase C (PKC) Activity in Isolated Membranes-Using a Selective Peptide Substrate." Anal. Biochem., 196, 144–150.

Chen, S-J, Klann, E., Gower, M. C., Powell, C. M., Sessoms, J. S., and Sweatt, J. D., 1993. "Studies with Synthetic Peptide Substrates Derived from the Neuronal Protein Neurogranin Reveal Structural Determinants of Potency and Selectivity for Protein-Kinase." C. Biochem., 32:1032–1039.

Gopalakrishna, Rayudu, Zhen H. Chen, Usha Gundimeda, John C. Wilson and Wayne B. Anderson, 1992, "Rapid Filtration Assays for Protein Kinase C Activity and Phorbol Ester Binding Using Multiwell Plates with Fitted Filtration Disks." Anal. Biochem., 206, 24–35.

Kemp, B. E. and Pearson, R. B., 1991. "Design and Use of Peptide Substrates for Protein Kinases." Meth. Enzymol., 200:121–134.

Rijksen, Gert, Brigit A. van Oirschot and Gerard E. J. Staal, 1991, "Nonradioactive Assays of Protein-Tyrosine Kinase Activity Using Anti-phosphotyrosine Antibodies." Methods in Enzymology, 200:98–107.

Robyt, John F. and Bernard J. White, 1990, Biochemical Techniques—Theory and Practice, Waveland Press, Inc., Prospect Heights, Ill., pp. 291–320.

What is claimed is:

1. A method of determining the presence or activity of a selected protein kinase, comprising:

a. providing a biotinylated peptide substrate containing a biotin moiety, wherein the biotin moiety is conjugated to the peptide substrate at its N-terminal amino group via a linker at least six carbon atoms in length;

b. adding a sufficient quantity of the biotinylated peptide substrate to a solution containing the selected protein kinase;

c. incubating the selected protein kinase with the biotinylated peptide substrate under conditions where the selected protein kinase is active for a time sufficient to form a phosphorylated, biotinylated peptide product;

d. binding the biotinylated peptide product to a biotin-binding matrix, wherein the matrix has a sufficient binding capacity and specificity for the biotinylated peptide product to capture essentially all of the biotinylated peptide substrate and biotinylated peptide product from solution; and e. detecting the presence and measuring the activity of the selected protein kinase.

2. The method of claim 1 wherein the matrix includes a protein selected from the group consisting of avidin and streptavidin.

3. The method of claim 1 further comprising washing the bound biotinylated peptide product prior to measuring the activity of the selected protein kinase.

4. The method of claim 1 wherein the matrix includes a membrane coated with a protein selected from the group consisting of avidin and streptavidin.

5. The method of claim 1 wherein the matrix includes beads coated with a protein selected from the group consisting of avidin and streptavidin.

6. The method of claim 1 wherein the selected protein kinase is incubated in the presence of the biotinylated peptide substrate and a label.

7. The method of claim 1 wherein the biotinylated peptide substrate can be any one of biotinylated SEQ. ID. NOS: 1 through 8.

8. The method of claim 1 wherein the selected protein kinase is selected from the group consisting of serine-threonine kinases and tyrosine kinases.

9. The method of claim 6 wherein the label is a radioactive label.

10. The method of claim 6 wherein a quantity of modified peptide product is measured by a scintillation spectrometer.

11. The method of claim 9 wherein the radioactive label is $\gamma$-$^{32}$P.

12. A kit for determining the presence or activity of a selected protein kinase comprising:

a. a container containing a biotinylated peptide substrate containing a biotin moiety; wherein the biotin moiety does not result in a steric hindrance of the biotinylated peptide substrates accessibility to the protein kinase, the biotinylated peptide substrate further having specific reactivity to the selected protein kinase and modified by chemical reaction to allow quantitation; and b. instructions for use.

13. The kit of claim 12 further including a container having at least one buffer which is compatible with the selected protein kinase.

14. The kit of claim 12 including a container containing a biotin-binding matrix.

15. The kit of claim 12 wherein the biotinylated peptide substrate can be any one of biotinylated SEQ. ID. NOS: 1 through 8.

16. The kit of claim 12 wherein the selected protein kinase is selected from the group consisting of serine-threonine kinases and tyrosine kinases.

17. A kit for determining the activity of a tyrosine kinase comprising:

a. a container containing a biotinylated peptide substrate as shown in SEQ. ID. NO: 7;

b. a container containing a biotin-binding matrix, wherein the biotin-binding matrix has a sufficient binding capacity and specificity for the tyrosine kinase-biotinylated peptide substrate; and c. instructions for use.

18. A kit for determining the presence or activity of serine-threonine kinases comprising:

a. a container containing a biotinylated peptide substrate which can be any one of biotinylated SEQ. ID. NOS: 1 through 8;

b. a container holding a biotin-binding matrix, wherein the biotin-binding matrix has a sufficient binding capacity and specificity for the biotinylated peptide substrate; and c. instructions for use.

* * * * *